United States Patent [19]

Hicks

[11] Patent Number: 4,784,175

[45] Date of Patent: Nov. 15, 1988

[54] VALVE

[75] Inventor: Richard B. Hicks, Kingston-upon-Thames, United Kingdom

[73] Assignee: Aerosol Medical Limited, London, England

[21] Appl. No.: 30,267

[22] Filed: Mar. 24, 1987

Related U.S. Application Data

[63] Continuation of Ser. No. 826,626, Feb. 6, 1986, abandoned.

[30] Foreign Application Priority Data

Mar. 4, 1985 [GB] United Kingdom ............... 8505433
Nov. 19, 1985 [GB] United Kingdom ............... 8528413

[51] Int. Cl.⁴ .............................................. F16K 31/22
[52] U.S. Cl. ..................................... 137/202; 137/519
[58] Field of Search ............... 137/199, 202, 205, 519

[56] References Cited

U.S. PATENT DOCUMENTS

| | | | |
|---|---|---|---|
| 430,448 | 6/1890 | Todd | 137/199 X |
| 570,073 | 10/1896 | Van Sickle | 137/202 |
| 812,451 | 2/1906 | Rice | 137/202 |
| 1,667,877 | 5/1928 | Star | 137/202 |
| 2,812,772 | 11/1957 | Moore | 137/202 |
| 2,908,282 | 10/1959 | Maisch | 137/199 |
| 2,988,102 | 6/1961 | Harry et al. | |
| 3,114,383 | 12/1963 | Myers | |
| 3,768,498 | 10/1973 | Urban | 137/202 X |
| 4,263,912 | 4/1981 | Adams | |
| 4,311,141 | 1/1982 | Diamond | |
| 4,474,189 | 10/1984 | Brown | |

FOREIGN PATENT DOCUMENTS

| | | |
|---|---|---|
| 0000339 | 1/1979 | European Pat. Off. |
| 531675 | 8/1931 | Fed. Rep. of Germany |
| 1028500 | 4/1958 | Fed. Rep. of Germany ...... 137/519 |
| 2819494 | 11/1978 | Fed. Rep. of Germany |
| 2751593 | 12/1978 | Fed. Rep. of Germany |
| 775136 | 5/1957 | United Kingdom |
| 2155792 | 10/1985 | United Kingdom |

Primary Examiner—Robert G. Nilson
Attorney, Agent, or Firm—Young & Thompson

[57] ABSTRACT

A valve is provided primarily for medical or surgical aspiration equipment. The valve is interposed in an air line between the low pressure side of a pump and a collecting bottle for body fluid. The valve chamber has a sump-like bottom in which any liquid or froth entrained in air drawn in at a higher position will collect, and the valve member defines with said bottom narrow air admission apertures which are readily occluded by such liquid or froth, thereby producing a pressure difference across the valve member which displaces it to the valve-closed position.

11 Claims, 2 Drawing Sheets

VALVE

This application is a continuation of application Ser. No. 826,626 filed 2-6-86 now abandoned.

BACKGROUND OF THE INVENTION

This invention relates to a valve and is particularly, although not exclusively, concerned with improvements in the type of valve used to prevent anything but air reaching a suction pump used in surgical or medical aspiration equipment.

Such equipment is used for a variety of purposes, such as the drainage of wounds or the collection of human milk. Typically it comprises a storage bottle for the fluid being drawn off and two tubes penetrating the lid of the bottle. One of the tubes opening to a lower position in the bottle leads e.g. to the wound being drained or can be connected to a human breast and the other tube, opening to a higher position in the bottle, leads to the low pressure side of an air pump. By displacing air out of the bottle body fluid is drawn into it. When the bottle is sufficiently filled the pump is stopped and the bottle sealed, if necessary being replaced by another one.

The utmost hygiene is, of course, vital in the use of such equipment, not only to prevent the transmission of disease between different patients using the same equipment, but to prevent escape into the environment, e.g. of a hospital ward, of micro-organisms from the output side of the pump. To quote from British Standard 4199: Part 2: 1968, "Surgical Suction Apparatus":

> "When infective material is being aspirated, the inevitable bubbling and splashing in the collecting bottle create a bacterial aerosol which passes into the pump and often from its exhaust outlet into the air of the room".

Measures to protect the pump, discussed in the same British Standard, include an "air leak needle valve" and a filter. It is not herein suggested that a filter should be dispensed with, but the inadequacy of a filter alone to cope with the problem is discussed in the British Standard. Because a filter will become wet ". . . if the bottle becomes filled with froth, and is not immediately changed, fluid is sucked through the filter and into the pump".

By an "air leak needle valve" the British Standard is believed to refer to a float valve of the kind used to control a carburettor, i.e. a buoyant body supporting the needle will float up on liquid entering the valve chamber until the needle engages a valve seat to close the valve. Float valves can take a variety of other forms of which the commonest, perhaps, comprises a captive ball which floats up in its cage to shut an air intake in the presence of liquid. Such a float valve, incorporated in a breast pump, is exemplified in British Patent Specification No. 2 155 792A.

Such float valves do not solve the present problem. They will close in the presence of sufficient liquid, but will allow e.g. fine bubbles or an aerosol dispersion to pass through to the pump without closing. A filter between the valve and the pump may not be effective to prevent infective material being blown out of the pump exhaust.

Furthermore, the most effective and commonly used method of sterilisation is by autoclaving. Known float valves are not suited to be subjected to high sterilising temperatures without danger of rupture.

SUMMARY OF THE INVENTION

A principal object of the present invention is to overcome these problems by the provision of a valve which will respond to the presence in the air line not only of liquid but also of froth, or indeed any medium of greater density than air.

Another object of the present invention is to provide such a valve the components of which can be subjected to high sterilising temperature without damage.

Another object of the present invention is to provide a valve for controlling the flow of a gaseous medium, the valve comprising a chamber having an outlet connectable to the low pressure side of a suction pump, a valve member having limited movement in the housing between a valve-open position in which the valve member is spaced from the outlet and a valve-closed position in which the valve member seals the outlet, the valve member being disposed between an inlet of the chamber for said medium and said outlet and being biased to the valve-open position in which there is a passage through the chamber for said medium between the inlet and outlet, at least partly defined by the valve member, wherein the valve member is of greater cross-sectional area than the passage in the same plane transverse to the direction of movement of the valve member, the arrangement being such that if the inlet or passage is obstructed by a greater-density medium the valve member will be displaced against its bias to the valve-closed position by the pressure drop across it produced by the pump.

Said bias of the valve member may be gravity which acts on the valve member in the valve-opening direction when the valve is upright.

The valve member when in the valve-open position preferably cooperates with the interior of the chamber to provide a restricted inlet whereby said medium entering the chamber is distributed around the periphery of the valve member. One or more formations of the valve member or of the chamber may serve to locate the valve member in a predetermined, spaced relation to an end of the chamber remote from the outlet when the valve member is in the valve-open position, the arrangement being such that said medium enters the chamber through the space or spaces between the valve member and said chamber end peripherally of the valve member.

The valve member is preferably hollow and means is preferably provided whereby the medium enters the chamber through the interior of the valve member.

Openings in a wall of the chamber and of the valve member may be in register throughout the permitted movement of the valve member and said medium may enter the chamber through said openings.

The valve member may be elongated and hollow and may have a closed end adapted to form a seal with said outlet when the valve is closed and an open end adapted to co-operate with the chamber to provide said inlet when the valve is open. The open end of the valve member may have circumferentially spaced projections which, when the valve is open, abut an end wall of the chamber remote from the outlet to provide restricted openings of predetermined dimensions between the valve member and said end wall, said openings constituting the inlet of the valve.

The chamber may have a tubular peripheral wall generally parallel with the peripheral wall of the valve member and formations of the valve member or of the chamber may maintain the valve member generally coaxial with respect to the chamber throughout the permitted movement of the valve member and concentric with respect to the outlet. Said formations may comprise fins projecting radially from the valve member in circumferentially spaced relation, each extending longitudinally of the valve member to make sliding contact with the inner periphery of the chamber.

An angularly separated pair of said fins are preferably positioned to locate on opposite sides of an indentation of the chamber periphery such that the valve member is maintained in a constant angular orientation relative to the chamber throughout the travel of the valve member.

The outlet is preferably in the form of a frusto-conical valve seat tapering outwardly of the chamber and the valve member preferably has located in an annular recess thereof a resilient sealing ring which, when the valve is closed, is brought into sealing engagement with said valve seat.

The valve member is preferably buoyant so that it will be displaced to the valve-closed position if sufficient liquid enters the chamber.

According to yet another aspect of the invention there is provided a valve for controlling the admission of a gaseous medium to the low pressure side of a pump, the valve comprising a valve chamber a bottom portion of which is designed to collect any medium of a greater density entering the valve, a hollow valve member movable up and down in the chamber to and from a valve-closed position in which a closed, upper end of the valve member occludes an outlet opening in the upper region of the valve chamber and means defining an inlet for the gaseous medium between the bottom of the valve chamber and the bottom of the valve member when the latter is in a lowered, valve-open position, the inlet being arranged and dimensioned to permit the free passage of said gaseous medium unless obstructed by a medium of greater density which has collected in said bottom portion of the valve chamber, wherein at least part of the outer periphery of the valve member is substantially parallel with the inner periphery of the chamber and forms therewith an annular passage around the valve member for the gaseous medium, which passage is of smaller cross-sectional area than the valve member and the arrangement being such that if, in use, the inlet is obstructed by a greater density medium the valve member will be raised to the valve-closed position by the pressure drop across it produced by the pump.

It is yet another object of the present invention to provide a valve for controlling the flow of a gaseous medium, the valve comprising a chamber having an outlet connectable to the low pressure side of a suction pump, a valve member having limited movement in the chamber between a valve-open position in which the valve member is spaced from a seat therefor to open the outlet and a valve-closed position in which the valve member seals the outlet, the valve member being disposed between an inlet for said medium and said outlet and being biased in the valve-open position in which there is a passage through the chamber for said medium between the inlet and the outlet at least partly defined by the valve member, said valve being characterised by the combination of features that the valve member is of greater cross-sectional area than the said passage in the same plane transverse to the direction of movement of the valve member and that the path for the incoming medium between said inlet and said passage is adapted to permit the free flow of said medium but to be occluded by a greater-density medium, the arrangement being such that if, in use, said inlet, path and/or passage is obstructed by a greater density medium the valve member will be displaced against its bias to the valve-closed position by the pressure drop across it produced by the pump.

BRIEF DESCRIPTION OF THE DRAWINGS

By way of non-limitative example embodiments of the invention are illustrated in the accompanying drawings. In the drawings.

DETAILED DESCRIPTION OF THE DRAWINGS

Figure 1:
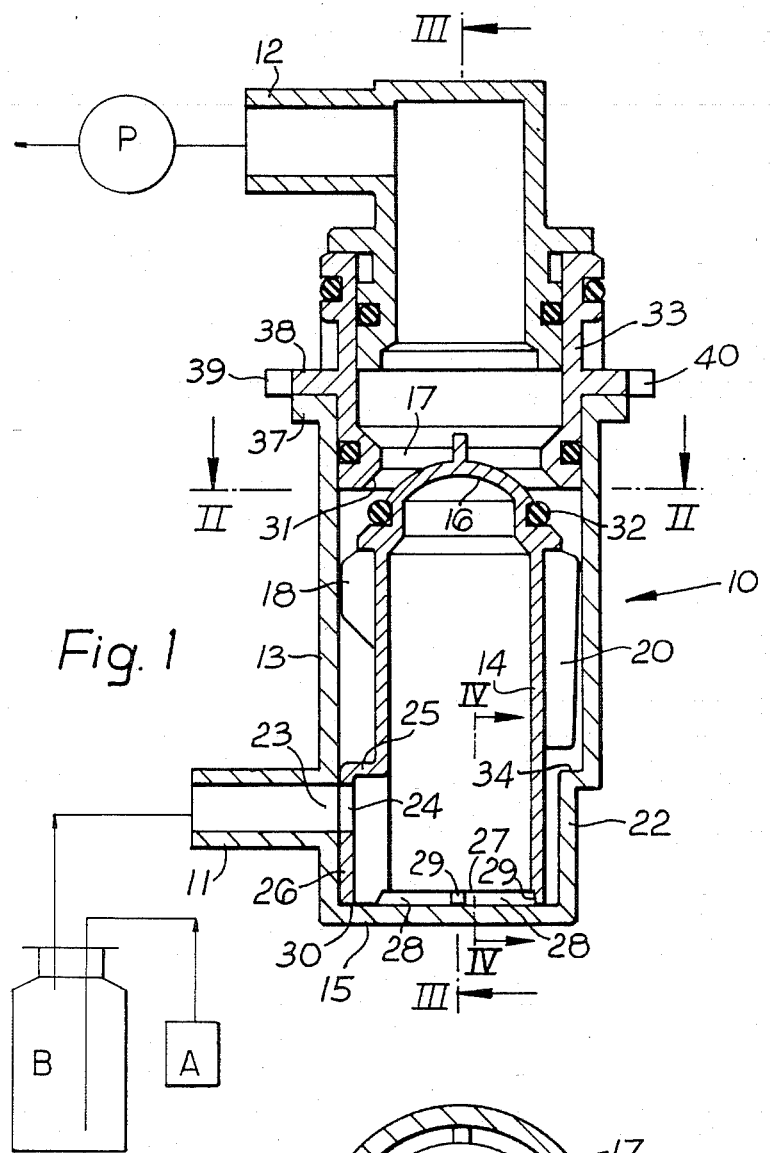
FIG. 1 is a sectional elevation of a valve in accordance with the present invention, taken on the line I—I of FIG. 3.
Figure 2:
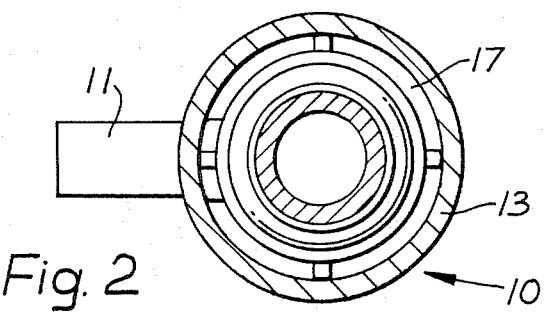
FIG. 2 is a cross-section taken on the line II—II of FIG. 1, as viewed in the direction of the arrows.

The valve assembly 10 illustrated is intended for inclusion in an air line between a collecting bottle B of medical or surgical aspiration apparatus A and a suction pump P. In use an inlet pipe 11 of the valve is connected to the bottle B and an outlet pipe 12 of the valve is connected to the low pressure side of the pump P. A filter (not shown) may be incorporated in the upper part of the valve housing or interposed between the outlet pipe 12 and the pump.

The valve 10 comprises a generally cylindrical chamber 13 in which an elongated valve member 14 is captive but which can move coaxially in the chamber between a valve-open position, in which it is shown and in which it rests on a bottom wall 15 of the chamber, and a raised, valve-closed position in which an upper end 16 of thee valve member closes an outlet opening 17 of the chamber. To guide the valve member 14 in its reciprocative movement in the chamber 13, to maintain it in concentric alignment with the outlet 17 and also to keep it positioned coaxially within the chamber so that there is a substantially constant-width free space between the outer periphery of the valve member 14 and the inner periphery of the chamber 13 the valve member 14 has radially-extending fins 18, 19A and B, 20 and 21A and B, distributed circumferentially around it and each elongated in a plane containing the axis of the valve member 14 so that the radially outer edges of the fins are in sliding contact with the inner periphery of the chamber.

Two of the fins at the bottom end of the valve member 14, namely the fins 19B and 21B locate, in use, on opposite sides of a protrusion 22 of the wall of the chamber 13 in the region of its bottom end. Thus the fins 19B and 21B prevent relative rotation of the valve member 14 and the chamber 13 and keep in alignment with one another, throughout the permitted movement of the valve member 14, the opening 23 in the chamber wall at the inner end of the pipe 11 and an opening 24 in the periphery of the valve member. This opening 24 is provided in a shoulder portion 25 projecting from the lower portion of the periphery of the valve member 14 and the outer surface 26 of the shoulder is shaped similarly to the inner periphery of the chamber 13 so as effectively to make a sliding seal against it.

The elongated valve member 14 is hollow, closed at its top end 16 and open at its bottom end 27. Thus air drawn into the valve member 14 through the registered openings 23 and 24 will emerge into the chamber 13 through an inlet which is defined by arcuate spaces 28 between the bottom, open end of the valve member 14 and the bottom 15 of the chamber. These spaces 28 are between projections 29 circumferentially separated around the open end 27 of the valve member and between the adjacent pair of projections 29 and the bottom edge 30 of the shoulder 25. Obviously, the extent of these projections 29 and the bottom edge 30 from the open end 27 of the valve member 14 and also their aggregate circumferential width determines the aggregate cross-sectional area of the inlet to the chamber 13 which the spaces 28 constitute when the valve member 14 rests on the bottom wall 15 of the chamber in the valve-open position as shown. It is also to be noted that this "inlet", constituted by a plurality of arcuate slits 28, distributes the incoming air more or less uniformly around the valve member 14, and that thereafter the air passes to the outlet 17 of the chamber 13 via an annular passage between the outer periphery of the valve member 14 and the inner periphery of the chamber 13 which is interrupted only by the narrow fins 18,19,20,21, the latter ensuring that the radial width of the passage is circumferentially uniform.

The outlet 17 of the chamber 13 is defined by a frusto-conical valve seat 31. When the valve member 14 rises to the valve-closed position the valve seat 31 is engaged by a resilient sealing ring 32 located in an annular recess in the closed end 16 of the valve member, so as to provide a good air seal.

From time to time the valve will be sterilised, preferably by autoclaving. For this purpose it is disassembled and subsequently reassembled. An upper part 33 of the assembly including the pipe 12 and the valve seat 31 is removed from the chamber 13, and thereafter the valve member 14 can be taken out through the open, upper end of the chamber. When the valve member 14 is re-inserted the fins 19B and 21B ensure that it will not be fully received into the chamber except in the correct angular orientation, viz with the openings 23 and 24 in register—otherwise one of them or the bottom edge 30 of the shoulder 25 will encounter the top edge 34 of the protrusion 22. This has sloping sides 35 and 36 so that if the valve member 14 is inserted only slightly misaligned one of the fins 19B and 21B will ride down one of the slopes 35 and 36 until the valve member 14 is rotated to the correct position.

The upper part 33 and the chamber 13 can be releasably held together in the position shown in any known suitable manner. Conveniently, for example, the chamber 13 (which is preferably transparent so that the ingress of froth, fluid or any other foreign matter can be monitored visually) may be partially surrounded by a mounting bracket (not shown) adapted for fixture to a wall or other support. This may engage the overlapping flanges 37 and 38 on the respective parts 33 and 13 in the manner of a bayonet fitting. If the assembly 13,33 is rotated in the bracket until bayonet arms (not shown) of the bracket register with diametrically opposite cut-away areas 39 and 40 of the larger of the two flanges they can both be lifted upwardly out of the bracket.

In use of the apparatus illustrated suction is applied to the pipe 12 while the pipe 11 is connected to a tube (not shown) entering an upper part of a collection bottle. At this time the valve member 14 is biased by gravity to the valve-open position shown. Air is drawn into the interior of the valve member 14 through the registered openings 23 and 24, passes into the chamber 13 through the slits 28, travels up the chamber 13 around the outside of the valve member 14 and exits to the pipe 12 through the outlet 17.

Figure 3:
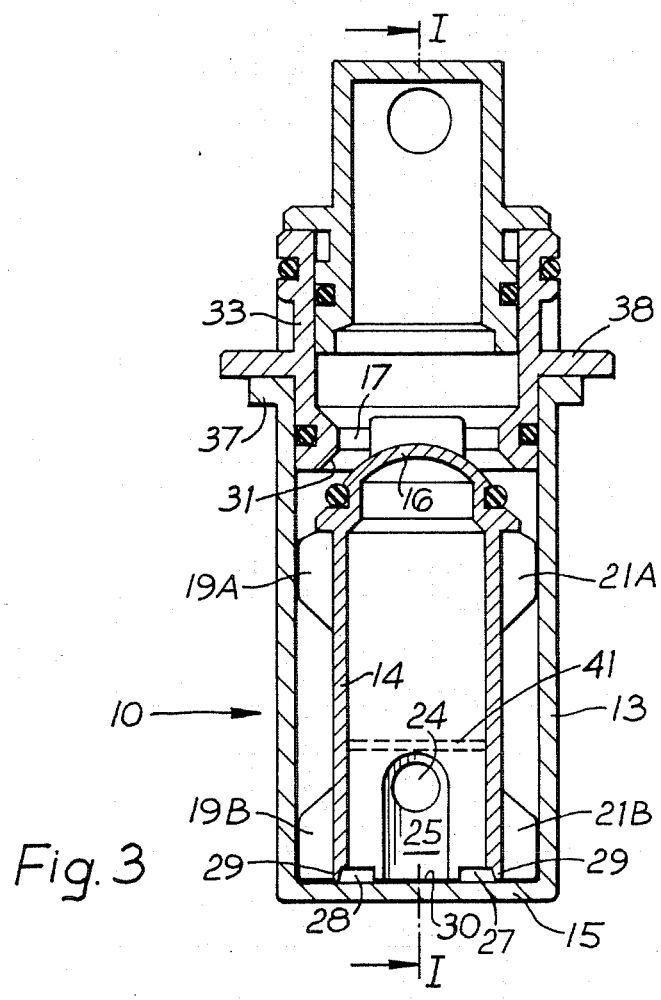
FIG. 3 is a sectional elevation taken on the line III—III of FIG. 1, a modification being indicated by the broken line 41.
Figure 4:
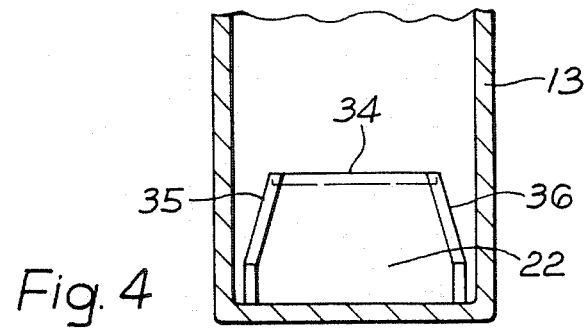
FIG. 4 is a fragmentary view of a protruding part of the chamber wall taken on the line IV—IV of FIG. 1 and with the valve member 14 removed.

Being air filled, the valve member 14 will tend to float in any liquid introduced into the chamber 13. To obviate the consequences of any freak occurrence resulting in the total or partial replacement by liquid of the air in the interior of the valve member 14, thus reducing its buoyancy, the latter is preferably inherently buoyant. Either it may be made from a buoyant material or means may be provided to trap in the valve member 14 air or another buoyancy aid. An example of such a modification is indicated in broken lines in FIG. 3, where a disc 41 is shown sealed at its periphery to the interior of the valve member, thus providing a sealed air space in the valve member 14 immediately above the opening 24.

However, the valve of the present invention, although also a float valve, is designed to close before there is sufficient liquid in the chamber to float it up to the valve-closed position. Because of the shape and disposition of the inlet slits 28, their relationship to the outlet space 17 and the fact that the cross-sectional area of the valve member 14 is greater than that of the passage for air which surrounds it, any occlusion of the slits 28 whether by liquid or by froth will cause a pressure drop across the valve member 14 which will lift it to the valve-closed position. The lifting of the valve member 14 will be virtually instantaneous, so that enlargement of the gap at its base as it rises is immaterial. In any event, in the preferred construction illustrated in which air enters the valve member 14 laterally through registered openings 23 and 24 when the valve member 14 is in the valve-open position the additional safeguard is obtained that as the valve member 14 rises to the valve-closed position the opening 24 moves out of register with the opening 23 so that air entry is progressively restricted. This restriction enhances the pressure drop across the valve member 14 and compensates for the increase of the gap at the bottom of the valve member. The valve member 14 will remain in the valve-closed position as long as there is sub-atmospheric pressure above its surface 16, i.e. as long as the pump remains active.

The shallow, narrow shape of the slits 28 facilitates their rapid occlusion by even a small quantity of even fine bubbles or froth. However, the operation of the valve is not dependent upon this preferred feature. Provided the cross-sectional area of any part of the passageway defined between the inner periphery of the chamber and the outer periphery of the valve member is less than the cross-sectional area of the parallel portion of the valve member 14 the obstruction by liquid, froth or any other medium denser than air of the inlet to the valve chamber will cause a pressure drop across the valve member 14 tending to close the valve.

It will be noted that the illustrated embodiment provides an arrangement whereby any liquid or froth entering the valve through the pipe 11 will fall into a sump or well defined by the bottom part of the valve chamber 13, where it will immediately tend to occlude the slits 28. To ensure that these are occluded by a minimum of liquid or froth their vertical extend should be no more than will ensure the unrestricted passage of air through the valve. Depending on the overall dimensions of the valve components and the capacity of the suction pump employed a suitable height (i.e. vertical extent) for the slits 28 will lie in the range 0.7 to 1.25 mm.

I claim:

1. An aspirator having an air outlet connected to an air inlet of a valve, the valve having an air outlet connected to an inlet of a gas pump, the valve comprising an upright chamber having said outlet in the region of its upper end, a sump-like formation spanning the bottom of the chamber adapted for the collection of liquid entering the chamber and to prevent escape of the same, a hollow valve member contained within said chamber and having a closed upper end and an open bottom end above said chamber bottom, the valve member having limited up-and-down movement in the housing between a lowered, valve-open position to which it is biassed by gravity and in which the valve member is spaced from the outlet and a raised, valve-closed position in which said closed end seals the outlet, said valve inlet opening to the interior of the valve member, end means defining a restricted flowpath for said medium through said valve member and said sump-like formation between said valve inlet and outlet in said valve-open position, said restricted flowpath means being arranged and dimensioned to be occluded by a greater density medium collecting in said sump-like formation, the cross-sectional area of the space between the exterior of the valve member and the interior of the chamber being less than that of the valve member in the same plane transverse to the direction of movement of the valve member, said restricted flowpath providing the sole communication between said valve inlet and said valve outlet in said valve-open position such that if, in use, said restricted flowpath is occluded the valve member will be raised to the valve-closed position by the pressure drop across it produced by the pump, the lower end of the valve member, when the valve is open, abutting an end wall of the chamber remote from the outlet, there being circumferentially-spaced projections on one of said lower end and said end wall that provide restricted openings of predetermined dimensions between the valve member and said end wall, said openings comprising said restricted flowpath.

2. A valve as claimed in claim 1, wherein the valve member when in the valve-open position co-operates with the interior of the chamber to provide said restricted flowpath whereby said medium entering the chamber is distributed around the periphery of the valve member.

3. A valve as claimed in claim 2, wherein one or more formations of the valve member or of the chamber serve to locate the valve member in a predetermined, spaced relation to said lower end of the chamber when the valve member is in the valve-open position, the arrangement being such that said medium enters the chamber through the space or spaces between the valve member and said chamber end peripherally of the valve member.

4. A valve as claimed in claim 1 wherein openings in a wall of the chamber and of the valve member are in register throughout the permitted movement of the valve member and wherein said medium enters the interior of the valve member through said openings.

5. A valve as claimed in claim 1, wherein the outlet is in the form of a frusto-conical valve seat tapering outwardly of the chamber and wherein the valve member has located in an annular recess thereof a resilient sealing ring which, when the valve is closed, is brought into sealing engagement with said valve seat.

6. A valve as claimed in claim 1, wherein the valve member is buoyant so that it will be displaced to the valve-closed position if sufficient liquid enters the chamber.

7. A valve as claimed in claim 1, in which said projections are on said lower end of the valve member.

8. An aspirator having an air outlet connected to an air inlet of a valve, the valve having an air outlet connected to an inlet of a gas pump, the valve comprising a chamber having said outlet and said inlet in spaced-apart relation, a sump-like formation with a closed bottom arranged for the collection and retention of liquid entering the chamber, a valve member above said closed bottom contained by and displaceable in the chamber between positions closing and opening said outlet, means biassing the valve member to the valve-open position, a space between the periphery of the valve member and the interior of the chamber which communicates the valve inlet and outlet, when the valve is open, and which is of smaller cross-sectional area than that of the vale member in the same plane transverse to the direction of movement of the valve member, and a restricted flowpath communicating said inlet with said space via said sump-like formation in the valve-open position, said restricted flowpath providing the sole communication between said inlet and said outlet in said valve-open position, whereby if a medium other than said gaseous medium occludes said restricted flowpath the valve member will be displaced to the valve-closed position, the lower end of the valve member, when the valve is open, abutting an end wall of the chamber remote from the outlet, there being circumferentially-spaced projections on one of said lower end and said end wall that provide restricted openings of predetermined dimensions between the valve member and said end wall, said openings comprising said restricted flowpath.

9. A valve as claimed in claim 8, wherein the valve member is hollow and has an open end which, in the valve-open position, is located in said sump, said restricted inlet flowpath comprising lateral openings in the wall of the chamber and of the valve member, means for maintaining said openings in register, and projections spaced circumferentially of the open end of the valve member thereby to provide restrictions in the flowpath between the interior of the valve member and said space via the sump-like formation when the valve member is in the valve-open position.

10. A valve as claimed in claim 8, in which said projections are on said lower end of the valve member.

11. A valve for controlling the flow of a gaseous medium, the valve comprising an upright chamber having an outlet in the region of its upper end connectable to the low pressure side of a pump, a sump-like formation spanning the lower end of the chamber adapted for the collection of liquid entering the chamber and to prevent escape of the same, a hollow valve member of smaller cross-sectional area than the cross-sectional area of the interior of the valve chamber to define an annular space therebetween, said space being smaller in cross sectional area than the cross-sectional area of the valve member, the valve member having a closed upper end and an open bottom end, the valve member being contained in the chamber and having limited up-and-down movement therein above said sump-like formation between a lowered, valve-open position to which it is biassed by gravity and in which the valve member is spaced from the outlet and a raised, valve-closed position in which said closed end seals the outlet, inlet means for said medium comprising a lateral protrusion of the wall of the valve member across said annular space in sliding contact with the inner periphery of the valve chamber and formed with an opening above said sump-like formation, an opening in the wall of the valve chamber in register with said opening in the protrusion of the valve member, and means for maintaining said openings of the valve member and chamber in register throughout the permitted movement of the valve member, said register means comprising an inward protrusion of the wall of the chamber, fin means projecting radially of the valve member across said annular space in sliding contact with the interior of the valve chamber, said fin means comprising a pair disposed on opposite sides of said inward protrusion of the valve chamber to maintain the valve member in a predetermined angular position relative to the valve chamber, and means defining a restricted flowpath for said medium through said sump-like formation between said inlet and outlet, said restricted flowpath means comprising circumferentially spaced projections from the open, bottom end of the valve member which, in the valve-open position, rest on the bottom of said sump-like formation to define between the valve member and the sump-like formation a plurality of arcuate slits, said slits being dimensioned to be occluded by a greater density medium collecting in said sump-like formation, thereby causing displacement of the valve member to the valve-closed position under the influence of the pump.

* * * * *